US008541072B2

United States Patent
Foley et al.

(10) Patent No.: US 8,541,072 B2
(45) Date of Patent: Sep. 24, 2013

(54) UV CURED HETEROGENEOUS INTERMEDIATE TRANSFER BELTS (ITB)

(75) Inventors: Geoffrey M. T. Foley, Fairport, NY (US); Jin Wu, Pittsford, NY (US); Satchidanand Mishra, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 790 days.

(21) Appl. No.: 12/624,589

(22) Filed: Nov. 24, 2009

(65) Prior Publication Data

US 2011/0123732 A1 May 26, 2011

(51) Int. Cl.
B32B 3/14 (2006.01)
B32B 3/16 (2006.01)
B41M 5/382 (2006.01)
B41M 5/52 (2006.01)

(52) U.S. Cl.
CPC ............ B41M 5/38257 (2013.01); B41M 5/52 (2013.01); B41M 5/5218 (2013.01)
USPC ................ 428/32.51; 428/32.29; 428/32.5; 428/32.12

(58) Field of Classification Search
CPC ... B41M 5/38257; B41M 5/52; B41M 5/5218
USPC ............... 428/32.51, 32.39, 32.5, 32.12
See application file for complete search history.

(56) References Cited

U.S. PATENT DOCUMENTS

| | | | | |
|---|---|---|---|---|
| 5,576,818 A * | 11/1996 | Badesha et al. | ............... | 399/308 |
| 5,804,301 A * | 9/1998 | Curatolo | ........................ | 428/352 |
| 2002/0099110 A1 * | 7/2002 | Norlin et al. | ..................... | 522/35 |
| 2003/0087175 A1 * | 5/2003 | Simpson et al. | ............. | 430/126 |
| 2003/0143362 A1 * | 7/2003 | Hsieh et al. | ...................... | 428/58 |
| 2005/0040371 A1 * | 2/2005 | Watanabe et al. | ............. | 252/500 |
| 2005/0090388 A1 * | 4/2005 | Kishi et al. | .................... | 502/182 |
| 2006/0038299 A1 * | 2/2006 | Hirakata et al. | ................ | 257/773 |
| 2007/0188585 A1 * | 8/2007 | Mochizuki et al. | ........... | 347/140 |
| 2008/0251771 A1 * | 10/2008 | Maxime et al. | .......... | 252/519.33 |
| 2011/0052841 A1 * | 3/2011 | Wu et al. | ....................... | 428/32.5 |
| 2011/0104467 A1 * | 5/2011 | Wu et al. | ....................... | 428/220 |

OTHER PUBLICATIONS

Chen et al., "Noncovalent Engineering of Carbon Nanotube Surfaces by Rigid, Functional, Conjugated Polymers", J.Am. Chem. Soc., vol. 124, No. 31, 9034 (2002).*

* cited by examiner

*Primary Examiner* — Betelhem Shewareged
(74) *Attorney, Agent, or Firm* — MH2 Technology Law Group LLP

(57) ABSTRACT

Exemplary embodiments provide an intermediate transfer member that can include a plurality of carbon nanotubes dispersed in an ultraviolet (UV) curable polymer in an amount to allow a bulk curing of the UV curable polymer and to provide the cured polymer an electrical resistivity and/or a mechanical modulus useful for electrostatographic devices and processes.

15 Claims, 2 Drawing Sheets

US 8,541,072 B2

UV CURED HETEROGENEOUS INTERMEDIATE TRANSFER BELTS (ITB)

FIELD OF USE

The present teachings relate generally to intermediate transfer members used for electrostatographic devices and, more particularly, to ultraviolet (UV) cured intermediate transfer members.

BACKGROUND

Conventional materials for intermediate transfer belts include conductive powders dispersed in polyimide resins. The polyimide resins include thermoplastic polyimide resins and thermosetting polyimide resins. The conductive powders include carbon black, acetylene black, polyaniline, stannic oxide, indium oxide, tin oxide, titanium oxide, antimony tin oxide, indium tin oxide, zinc oxide, potassium titanate and other types of conductive/semi-conductive powders.

Although conventional polyimide-based intermediate transfer belts can be made seamed or even seamless, controlling uniformity of electrical resistivity and other properties is a challenge, due to variations in powder size, in powder concentration, and in milling process during the belt formation. In addition, conventional polyimide-based intermediate transfer belts are usually thermally cured at high temperatures greater than 350° C. for more than 1 hour. Coating solvents are then removed and are often released to environments in order to form the belt. However, faster and cleaner processes are desirable to fabricate intermediate transfer belts.

Thus, there is a need to overcome these and other problems of the prior art and to provide an intermediate transfer member containing UV curable polymers and carbon nanotubes.

SUMMARY

According to various embodiments, the present teachings include an intermediate transfer member. Specifically, the intermediate transfer member can include an ultraviolet (UV) curable polymer, a photoinitiator being capable of initiating a curing of the UV curable polymer; and a plurality of carbon nanotubes dispersed in the UV curable polymer in an amount sufficient to provide the cured UV polymer a surface resistivity ranging of about $10^8$ ohms/sq to about $10^{13}$ ohms/sq. In embodiments, the UV curable polymer can include a urethane acrylate and the plurality of carbon nanotubes can be about 3% or less by weight of the cured polymer.

According to various embodiments, the present teachings also include an apparatus for forming an image. The image-forming apparatus can include an imaging station and an intermediate transfer member. The imaging station can further include an image receiving member and at least one developing station that produces a developed toner image on the image receiving member. The intermediate transfer member can be used for receiving the developed toner image from the image receiving member, and transferring the developed toner image to an image receiving substrate.

The intermediate transfer member can further include a plurality of carbon nanotubes dispersed in an ultraviolet (UV) cured polymer in an amount of about 3% or less by weight. As a result, the cured polymer can have a surface resistivity ranging from about $10^8$ ohms/sq to about $10^{13}$ ohms/sq.

It is to be understood that both the foregoing general description and the following detailed description are exemplary and explanatory only and are not restrictive of the present teachings, as claimed.

BRIEF DESCRIPTION OF THE DRAWINGS

The accompanying drawings, which are incorporated in and constitute a part of this specification, illustrate several embodiments of the present teachings and together with the description, serve to explain the principles of the present teachings.

It should be noted that some details of the FIGS. have been simplified and are drawn to facilitate understanding of the embodiments rather than to maintain strict structural accuracy, detail, and scale.

DESCRIPTION OF THE EMBODIMENTS

Reference will now be made in detail to embodiments of the present teachings, examples of which are illustrated in the accompanying drawings. Wherever possible, the same reference numbers will be used throughout the drawings to refer to the same or like parts. In the following description, reference is made to the accompanying drawings that form a part thereof, and in which is shown by way of illustration specific exemplary embodiments in which the present teachings may be practiced. These embodiments are described in sufficient detail to enable those skilled in the art to practice the present teachings and it is to be understood that other embodiments may be utilized and that changes may be made without departing from the scope of the present teachings. The following description is, therefore, merely exemplary.

Exemplary embodiments provide an intermediate transfer member used for electrostatographic devices and processes. In embodiments, the disclosed intermediate transfer member can include one or more ultraviolet (UV) curable polymers, in contrast to conventional intermediate transfer members that use thermally cured polyimide resins. In embodiments, the disclosed intermediate transfer member can include a plurality of carbon nanotubes dispersed in the UV curable polymers in an amount to allow a bulk curing of the UV curable polymers and to provide the cured polymers with desired properties useful for the intermediate transfer member.

In embodiments, the use of UV curable polymers and related UV curing processes can provide many advantages including, for example, low manufacturing cost, high production efficiencies such as having a short curing process, and low VOC (volatile organic compounds). In an additional example, the UV cured materials for the exemplary intermediate transfer members can provide unique physical properties including, for example, resistance to stains, abrasions and solvents, coupled with superior toughness, and high gloss. Further, in embodiments, the UV cured materials for intermediate transfer members can be fabricated as seamless belts.

Figure 1:
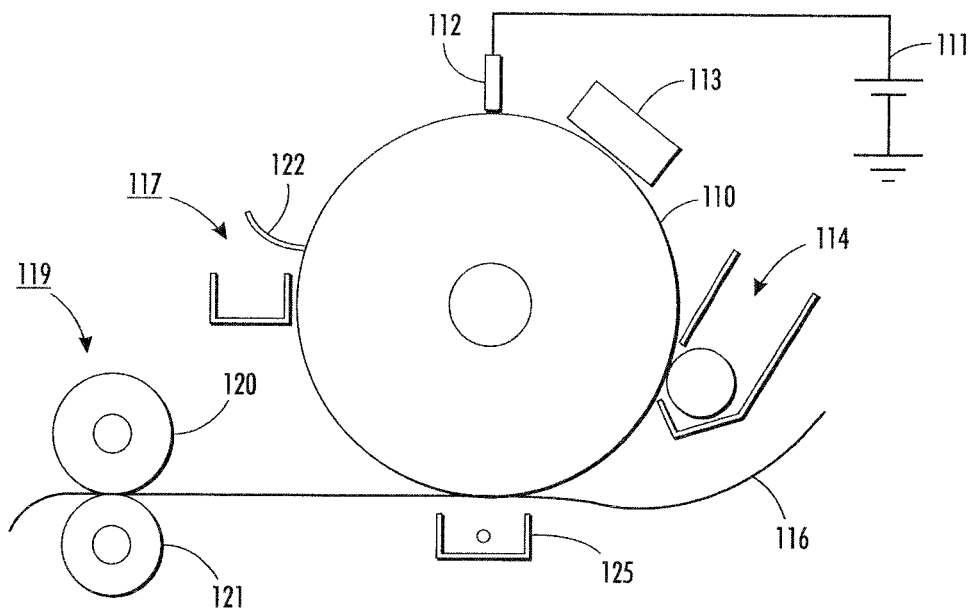
FIG. 1 depicts a general electrostatographic apparatus.

FIG. 1 depicts a general electrostatographic apparatus, wherein an intermediate transfer member is used. As known in the art of electrostatographic reproducing apparatus, a light image of an original to be copied can be recorded in the form of an electrostatic latent image upon a photosensitive member and the latent image can be subsequently rendered visible by the application of electroscopic thermoplastic resin particles, commonly referred to as toner.

Specifically, as shown in FIG. 1, photoreceptor 110 can be charged on its surface by means of a charger 112 to which a voltage can be supplied from a power supply 111. The photoreceptor 110 can then be image-wise exposed to light from an optical system or an image input apparatus 113, such as a laser and light emitting diode, to form an electrostatic latent image thereon. Generally, the electrostatic latent image can be developed by bringing a developer mixture from developer station 114 into contact therewith. Development can be effected by use of a magnetic brush, powder cloud, or other known development process.

After the toner particles have been deposited on the photoconductive surface, they can be transferred to a copy sheet 116 by a transfer means 125, which can be pressure transfer or electrostatic transfer. Alternatively, the developed image can be transferred to an intermediate transfer member and subsequently transferred to a copy sheet.

After the transfer of the developed image is completed, copy sheet 116 can advance to fusing station 119, depicted in FIG. 1 as fusing and pressure rolls (120/121), wherein the developed image can be fused to the copy sheet 116 by passing the copy sheet 116 between the fusing member 120 and pressure member 121, thereby forming a permanent image. Photoreceptor 110, subsequent to transfer, can advance to a cleaning station 117, wherein any toner left on the photoreceptor 110 can be cleaned there-from by use of a blade 122 (see FIG. 1), brush, or other cleaning apparatus.

Figure 2:
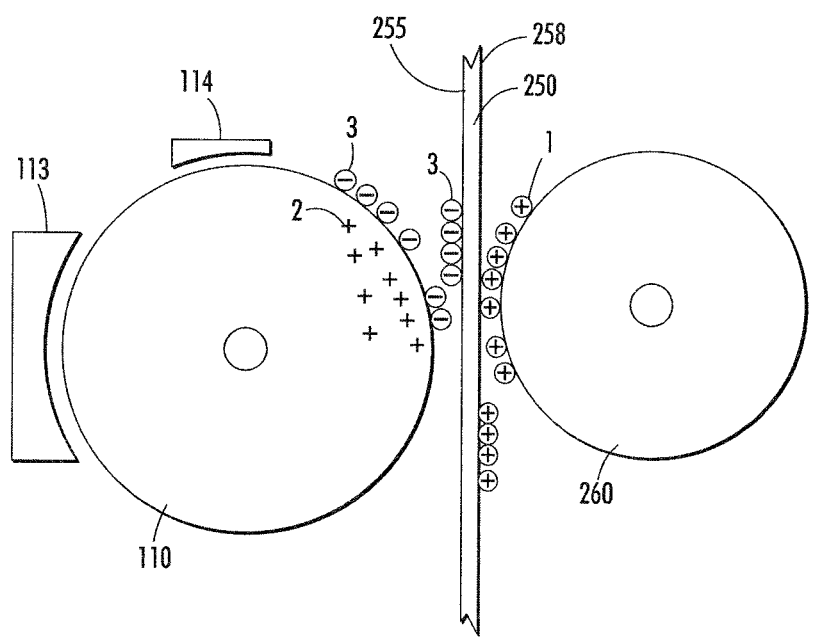
FIG. 2 depicts an exemplary image development system including an intermediate transfer member in accordance with various embodiments of the present teachings.

FIG. 2 depicts an exemplary image development system including an intermediate transfer member 250 in accordance with various embodiments of the present teachings.

As shown, the exemplary intermediate transfer member 250 can be positioned between an imaging member 110 and a transfer roller 260. The imaging member 110 can be exemplified by a photoreceptor drum. However, other electrostatographic imaging receptors such as ionographic belts and drums, electrophotographic belts, and the like can also be used.

Subsequent to development, the charged toner particles 3 from the developing station 114 can be attracted and held by the photoreceptor drum 110 because the photoreceptor drum 110 can possess a charge 2 opposite to that of the toner particles 3. In FIG. 2, the toner particles are shown as negatively charged and the photoreceptor drum 110 can be shown as positively charged. These charges can be reversed, depending on the nature of the toner and the machinery being used. In some embodiments, the toner can be present in a liquid developer. In other embodiments, dry development systems can also be used.

In embodiments, the intermediate transfer member 250 can be charged with a positive charge by, for example, a biased transfer roller, a corona or any other charging mechanism (not illustrated) having a higher voltage than the surface of the photoreceptor drum 110. The negatively charged toner particles 3 can be attracted to the front side 255 of the intermediate transfer member 250 by the positive charge 1 on the backside 258 of the intermediate transfer member 250.

After the toner latent image has been transferred from the photoreceptor drum 110 to the intermediate transfer member 250, the intermediate transfer member 250 can be contacted under heat and pressure to an image receiving substrate such as paper. The toner image on the intermediate transfer member 250 can then be transferred and fixed, to the image receiving substrate.

In embodiments, the intermediate transfer member 250 can be of any suitable configuration. Examples of suitable configurations can include a sheet, a film, a web, a foil, a strip, a coil, a cylinder, a drum, a drelt, a roller, an endless strip, a circular disc, a belt including an endless belt, an endless seamed flexible belt, an endless seamless flexible belt, an endless belt having a puzzle cut seam, and the like. For example, the intermediate transfer member 250 can be an endless seamed flexible belt or seamed flexible belt.

In embodiments, the intermediate transfer member 250 in a film or belt configuration can have, for example, from 1 to 3 or more layers. In embodiments, the circumference of the intermediate transfer member 250 in a film or belt configuration can range from about 8 to about 60 inches, or from about 10 to about 50 inches, or from about 15 to about 35 inches. The width of the film or belt configuration can range from about 8 to about 40 inches, or from about 10 to about 36 inches, or from about 10 to about 24 inches.

Figure 3A:
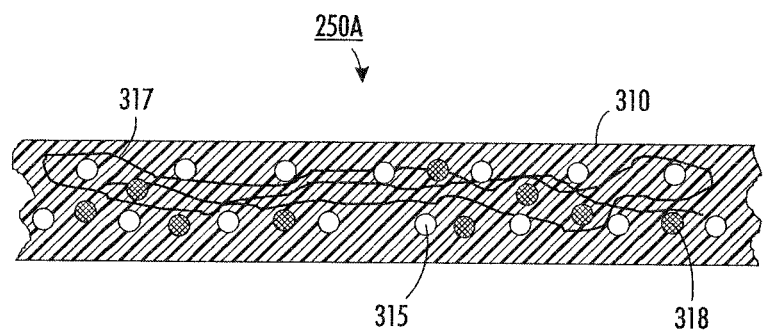
FIG. 3A depicts an exemplary intermediate transfer member in accordance with various embodiments of the present teachings.
Figure 3B:
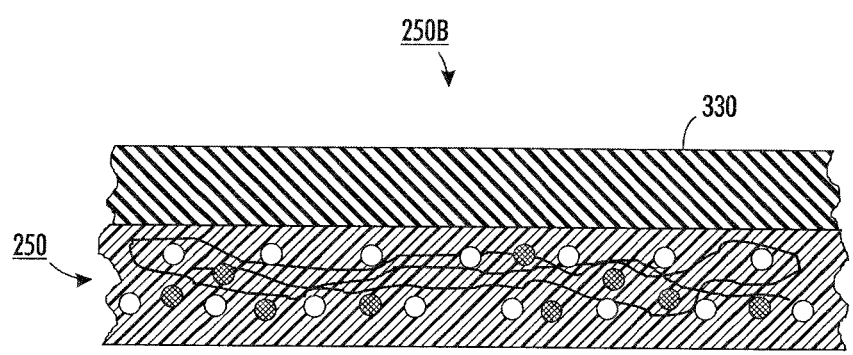
FIG. 3B depicts another exemplary intermediate transfer member in accordance with various embodiments of the present teachings.
Figure 3C:
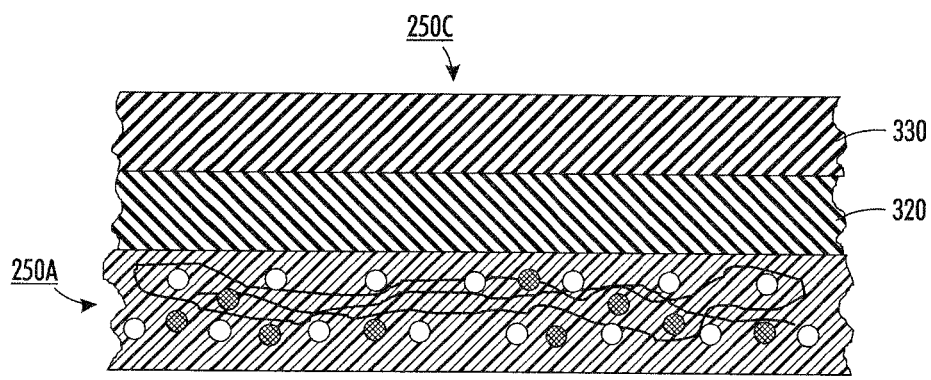
FIG. 3C depicts an additional exemplary intermediate transfer member in accordance with various embodiments of the present teachings.

FIG. 3A depicts an exemplary intermediate transfer member 250A having a single layer configuration, while FIGS. 3B-3C depict additional exemplary intermediate transfer members 250B-C having multi-layer configurations in accordance with various embodiments of the present teachings.

Specifically, the single layer of intermediate transfer member 250A, which is also referred to herein as intermediate transfer layer 250A, can be used as a substrate for the multi-layer configurations. For example, the intermediate transfer member 250B of FIG. 3B can include a two-layer configuration having an outer release layer 330 positioned on the intermediate transfer layer 250A.

In another example, the intermediate transfer member 250C of FIG. 3C can include a three-layer configuration including an outer release layer 330 positioned on a conformable layer 320, that is positioned on the intermediate transfer layer 250A. In embodiments, other additional functional layers, for example, adhesive layers, can be formed over the intermediate transfer layer 250A.

The outer release layer 330 shown in FIGS. 3B-3C can have a thickness ranging from about 0.1 to about 10 mil, or from about 0.5 to about 8 mil, or from about 1 to about 5 mil. Exemplary materials of the outer release layer 330 can include polymers suitable for release such as fluoropolymers.

Examples of the fluoropolymers can include fluoroplastics and/or fluoroelastomers. Fluoroplastics can include, for example, TEFLON®-like materials such as, fluorinated ethylene propylene copolymer (FEP), polytetrafluoroethylene (PTFE), and/or polyfluoroalkoxy polytetrafluoroethylene (PFA TEFLON®). Examples of the fluoroelastomers can include, for example, copolymers and terpolymers of vinylidenefluoride, hexafluoropropylene, and tetrafluoroethylene, which are commercially known under various designations as VITON A®, VITON E®, VITON E60C®, VITON E45®, VITON E430®, VITON B910®, VITON GH®, VITON B50®, VITON E45®, and VITON GF®. The VITON® designation is a Trademark of E.I. DuPont de Nemours, Inc. Among those, two known fluoroelastomers can include (1) a class of copolymers of vinylidenefluoride, hexafluoropropylene, and tetrafluoroethylene, known commercially as VITON A®; (2) a class of terpolymers of vinylidenefluoride, hexafluoropropylene, and tetrafluoroethylene, known commercially as VITON B®; and (3) a class of tetrapolymers of vinylidenefluoride, hexafluoropropylene, tetrafluoroethylene, and a cure site monomer, such as VITON GF®, having 35 mole percent of vinylidenefluoride, 34 mole percent of hexafluoropropylene, and 29 mole percent of tetrafluoroethylene with 2 percent cure site monomer. The cure site monomer can also include those available from E.I. DuPont de Nemours, Inc. such as 4-bromoperfluorobutene-1,1,1-dihydro-4-bromoperfluorobutene-1,3-bromoperfluoropropene-1,1,1-dihydro-3-bromoperfluoropropene-1, or any other suitable, known, commercially available cure site monomers.

As shown in FIG. 3C, the conformable layer 320 can have a thickness ranging from about 0.1 to about 20 mils, or from about 0.5 to about 10 mils, or from about 1 to about 5 mils. In embodiments, the conformable layer 320 can be made of, for example, silicone materials as known to one of ordinary skill in the art. Examples of the silicone materials can include fluorosilicones and silicone rubbers, such as silicone rubber 552, available from Sampson Coatings (Richmond, Va.).

As shown in FIGS. 3A-3C, the single layer of the intermediate transfer member 250A can include a plurality of carbon nanotubes 315 dispersed in a UV curable polymer 310. In addition, photoinitiators 318 can be included for initiating the photo-induced curing process of the UV curable polymer 310.

The carbon nanotubes (CNTs) 315 can have at least one minor dimension, for example, width or diameter, of about 100 nanometers or less. In embodiments, the carbon nanotubes 315 can include, for example, single-walled carbon nanotubes (SWCNTs), multi-walled carbon nanotubes (MWCNTs) and a combination thereof. Further, the CNTs can have various cross sectional shapes, such as, for example, rectangular, polygonal, oval, or circular shape. Accordingly, the CNTs can have, for example, cylindrical 3-dimensional shapes.

Note that although the term "nanotubes" is used throughout the description herein for illustrative purposes, it is intended that the term also encompass other elongated structures of like dimensions including, but not limited to, nanoshafts, nanopillars, nanowires, nanorods, and nanoneedles and their various functionalized and derivatized fibril forms, which include nanofibers with exemplary forms of thread, yarn, fabrics, etc.

The carbon nanotubes can provide desired functions, such as, mechanical, electrical (e.g., conductivity), and thermal (e.g., conductivity) functions to the disclosed intermediate transfer layer 250A of FIGS. 3A-3C. In addition, the nanotubes can be modified/functionalized nanotubes with controlled and/or increased mechanical, electrical or thermal properties through various physical and/or chemical modifications. Further, carbon nanotubes can be well dispersed as compared with other conventional conductive fillers such as carbon blacks.

Due to these unique properties, a small amount of carbon nanotubes can be sufficient to provide the disclosed intermediate transfer layer 250A of FIGS. 3A-3C with desired electrical, mechanical and/or other properties useful for electrostatographic devices and processes.

In embodiments, the carbon nanotubes 315 can be present in an amount of about 3% or less, or about 2% or less, or about 1% or less by weight of the total UV-cured polymer or the total intermediate transfer layer 250A of FIGS. 3A-3C.

In addition, this small but sufficient amount of the CNTs can allow UV radiation to penetrate through the entire UV curable polymer 310 for a complete curing or a desired curing extent to form the intermediate transfer layer 250A of FIGS. 3A-3C.

In comparison, conventional conductive fillers such as carbon blacks require high loading of about 3-20% by weight for conventional intermediate transfer members in order to achieve comparable electrical resistivity. This high-loading is not suitable for the disclosed UV curable polymers, because high-loaded carbon blacks may prevent UV light from penetrating deep into the UV curable polymer and cause an undesirable or incomplete curing of the polymer.

In embodiments, the disclosed intermediate transfer layer 250A of FIGS. 3A-3C can further include a dispersant 317 in connection with CNTs. For example, prior to forming the intermediate transfer members, CNTs can first be dispersed, for example, exfoliated and/or de-bundled, with an assistance of dispersants 317 in a suitable solvent. Such exfoliating and/or de-bundling processes can provide CNTs with high conductivity and high transparency.

In embodiments, the dispersant 317 can be present in the CNT-dispersant-based dispersion in an amount ranging from about 1% to about 40%, or from about 5% to about 30%, or from about 10% to about 20% by weight of the CNTs.

In embodiments, exemplary dispersants can have the following formula I:

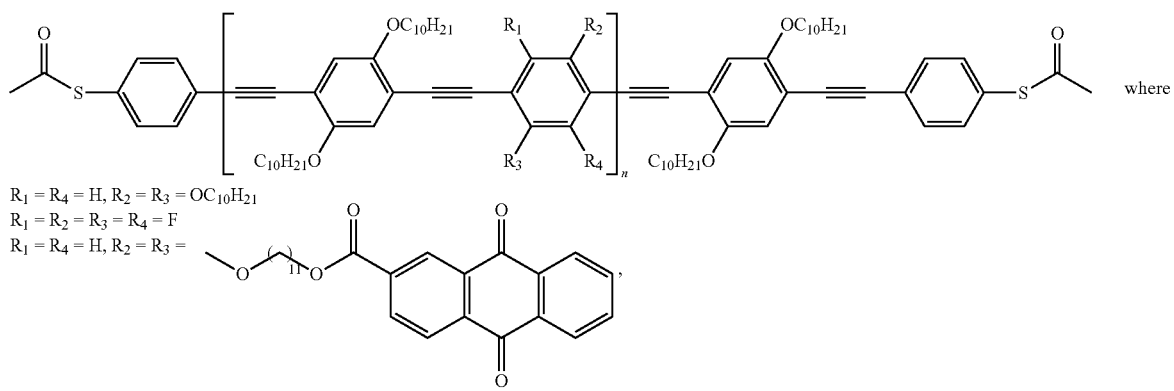

and where F is a halide including, for example, fluoride, chloride, bromide, or iodide; and n represents the number of repeating segments and ranges from about 1 to about 225, from about 5 to about 100; from about 50 to about 125, from about 10 to about 75, and the like.

In embodiments, exemplary dispersants can have the following formula II:

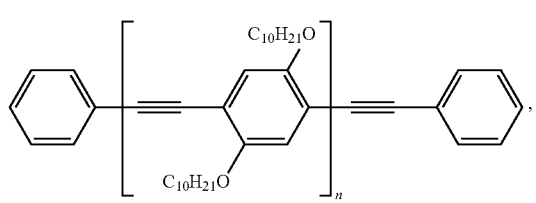

where n represents the number of repeating segments and ranges from about 1 to about 225, from about 5 to about 100; from about 50 to about 125, from about 10 to about 75, and the like.

In embodiments, the UV curable polymer 310 can include, for example, a urethane acrylate. Examples of the urethane acrylates can include aromatic urethane acrylates and aliphatic urethane acrylates and their mixtures thereof.

Specific examples of the aromatic urethane acrylates can include CN2901 an aromatic urethane triacrylate oligomer (Tg=35° C.); CN2902 an aromatic urethane triacrylate oligomer (Tg=25° C.); CN9782 a difunctional aromatic urethane acrylate oligomer; CN9783 a difunctional aromatic urethane acrylate oligomer; CN992 an aromatic polyester based urethane diacrylate oligomer; CN994 an aromatic urethane acrylate oligomer (Tg=50° C.); CN999 a low viscosity aromatic urethane oligomer (Tg=97° C.); CN997 a hexafunctional aromatic urethane acrylate oligomer; CN2600 a brominated aromatic urethane acrylate oligomer (Tg=88.8° C.); CN902J75 a brominated urethane acrylate oligomer containing 25% isobornyl acrylate; CN975 a hexafunctional aromatic urethane acrylate oligomer (Tg=-12° C.); CN978 an aromatic polyether based urethane diacrylate oligomer (Tg=-40° C.); CN972 an aromatic polyether based urethane triacrylate oligomer (Tg=-47° C.); CN9022 a urethane acrylate ester (Tg=-16° C.), all available from Sartomer Company, Inc., (Exton, Pa.); and LAROMER® UA 9031V, available from BASF (Ludwigshafen, Germany).

Specific examples of the aliphatic urethane acrylates can include CN9002 a difunctional aliphatic urethane acrylate oligomer; CN9004 a difunctional aliphatic urethane acrylate oligomer; CN9005 a difunctional aliphatic urethane acrylate oligomer (Tg=-10° C.); CN9006 a hexafunctional aliphatic urethane acrylate oligomer (Tg=83° C.); CN9007 a difunctional aliphatic urethane acrylate oligomer; CN9178 a difunctional aliphatic urethane acrylate oligomer; CN9290US a difunctional aliphatic urethane acrylate oligomer (Tg=-28° C.); CN940 a difunctional aliphatic urethane oligomer; CN9788 a difunctional aliphatic urethane oligomer; CN989 a trifunctional aliphatic urethane acrylate oligomer; CN9893 a difunctional aliphatic urethane oligomer; CN996 a urethane acrylate oligomer; CN9009 an aliphatic urethane acrylate oligomer (Tg=40° C.); CN9010 an aliphatic urethane acrylate oligomer (Tg=103° C.); CN3211 an aliphatic urethane acrylate oligomer; CN9001 an aliphatic urethane acrylate oligomer (Tg=60° C.); CN2920 an aliphatic urethane acrylate oligomer (Tg=59° C.); CN9011 an aliphatic urethane oligomer; CN929 a trifunctional aliphatic polyester urethane acrylate oligomer (Tg=17° C.); CN962 an aliphatic polyester based urethane diacrylate oligomer (Tg=-38° C.); CN965 an aliphatic polyester based urethane diacrylate oligomer (Tg=-37° C.); CN991 an aliphatic polyester based urethane diacrylate oligomer; CN980 a urethane acrylate oligomer (Tg=-29° C.); CN-981 an aliphatic polyester/polyether based urethane diacrylate oligomer (Tg=22° C.); CN964 an aliphatic polyester based urethane diacrylate oligomer (Tg=-24° C.); CN968 an aliphatic polyester based urethane hexaacrylate oligomer (Tg=34° C.); CN983 an aliphatic polyester based urethane diacrylate oligomer; CN984 an aliphatic polyester based urethane diacrylate oligomer; CN9008 a trifunctional aliphatic polyester urethane acrylate oligomer (Tg=111° C.); CN9024 an aliphatic urethane acrylate; CN9013 a multifunctional urethane acrylate oligomer (Tg=143° C.); CN9014, an aliphatic urethane acrylate oligomer (Tg=-41° C.), all available from Sartomer Company, Inc., (Exton, Pa.); and LAROMER® UA 19T, UA 9028V, UA 9030V, LR 8987, UA 9029V, and UA 9033V, all available from BASF (Ludwigshafen, Germany).

In embodiments, the UV curable polymer 310 can include viscous liquid oligomeric polymers having a molecular weight ranging from several hundreds to several thousands or even higher. For example, the UV curable urethane acrylates can have a molecular weight ranging from about 300 to about 5,000, or from about 500 to about 3,000, or from about 700 to about 2,000.

In embodiments, the exemplary UV curable urethane acrylates can possess a glass transition temperature (Tg) of from about -80° C. to about 200° C., or from about -40° C. to about 150° C., or from about 0 to about 100° C.

In embodiments, the UV curable polymer 310 can further include monomeric acrylates or vinyls, which can be admixed with oligomeric urethane acrylates. For example, monomeric acrylates or vinyls can function as co-reactants, and/or as diluents in the formulation so as to adjust the system viscosity.

In embodiments, the monomeric acrylates or vinyls can include, for example, LAROMER® TMPTA (trimethylolpropane triacrylate), BDDA (butandiol diacrylate), HDDA (hexandiol diacrylate), TPGDA (tripropyleneglycol diacrylate), DPGDA (dipropyleneglycol diacrylate), POEA (phenoxyethyl acrylate), LR8887 (trimethylolpropaneformal monoacrylate), TBCH (4-t-butylcyclohexyl acrylate), LA (lauryl acrylate 12/14), EDGA (ethyldiglycol acrylate), BDMA (butandiol monoacrylate), DCPA (dihydrodicyclopentadienyl acrylate), DVE-3 (triethyleneglycol divinyl ether), vinyl caprolactam, n-vinyl formamide, all available from BASF; and CN4000 (fluorinated acrylate oligomer), available from Sartomer Co. (Warrington, Pa.), and their combinations.

In embodiments, the intermediate transfer layer 250A of FIGS. 3A-3C can also include photoinitiators 318 for initiating a curing process of the UV curable polymer 310 including, for example, oligomeric urethane acrylates, or in some cases, also including monomeric acrylates or vinyls.

In embodiments, the photoinitiators 318 can include, for example, a photoinitiator for a surface curing of the UV curable polymer 310, a photoinitiator for a bulk curing through the UV curable polymer 310, and combinations thereof. In an exemplary embodiment, combined photoinitiators can be used to initiate the curing process the exemplary urethane acrylates.

Examples of the photoinitiators can include but are not limited to acyl phosphines, a-hydroxyketones, benzyl ketals, a-aminoketones, and mixtures thereof.

Examples of the acyl phosphine photoinitiators can include mono acyl phosphine oxide (MAPO) such as DAROCUR® TPO; and bis acyl phosphine oxide (BAPO) such as IRGACURE® 819, both available from Ciba Specialty Chemicals (Tarrytown, N.Y.).

Specific examples of the acyl phosphine photoinitiators can include diphenyl (2,4,6-trimethylbenzoyl)phosphine oxide (DAROCUR® TPO), diphenyl(2,4,6-trimethylbenzoyl)phosphine oxide (ESACURE® TPO, LAMBERTI Chemical Specialties, Gallarate, Italy), diphenyl(2,4,6-trimethylbenzoyl)phosphine oxide (FIRSTCURE® HMPP available from Albemarle Corporation, Baton Rouge, La.), diphenyl(2,4,6-trimethylbenzoyl)phosphine oxide (LUCIRIN® TPO, available from BASF (Ludwigshafen, Germany), diphenyl(2,4,6-trimethylbenzoyl)phosphinate (LUCIRIN® TPO-L), and phenyl bis(2,4,6-trimethyl benzoyl)phosphine oxide (IRGACURE® 819, available from Ciba Specialty Chemicals).

Examples of the a-hydroxyketone photoinitiators can include 1-hydroxy-cyclohexylphenyl ketone (IRGACURE® 184), 2-hydroxy-2-methyl-1-phenyl-1-propanone (DAROCUR® 1173), and 2-hydroxy-1-[4-(2-hydroxyethoxy)phenyl]-2-methyl-1-propanone (IRGACURE® 2959), all available from Ciba Specialty Chemicals.

Examples of the a-aminoketones photoinitiators can include 2-benzyl-2-(dimethylamino)-1-[4-(4-morpholinyl) phenyl]-1-butanone (IRGACURE® 369), and 2-methyl-1-

[4-(methylthio)phenyl]-2-(4-morpholinyl)-1-propanone (IRGACURE® 907), both available from Ciba Specialty Chemicals.

Examples of the benzyl ketal photoinitiators can include a,a-dimethoxy-a-phenylacetophenone (IRGACURE® 651), available from Ciba Specialty Chemicals.

In embodiments, the photoinitiators 318 can be in a form of, for example, crystalline powders and/or a liquid. In embodiments, the photoinitiators 318 can be present in an amount sufficient to initiate the curing process of the UV curable polymer 310. In embodiments, the photoinitiators 318 can be present in an amount ranging from about 0.5% to about 10%, or from about 10% to about 7%, or from about 2% to about 5% by weight of the UV curable polymer 310 or by weight of the total formed intermediate transfer layer 250A.

In embodiments, the disclosed intermediate transfer layer 250A of FIGS. 3A-3C can be prepared by, for example, first forming a liquid dispersion.

The liquid dispersion can include carbon nanotubes (CNTs) 315, a UV curable polymer 310, and photoinitiators 318. In embodiments, the CNTs can first be dispersed with a dispersant 317 to form a CNT-based dispersion. This CNT-based dispersion can then be dispersed with the UV curable polymer 310 and/or the photoinitiators 318 to form the liquid dispersion. Because the UV curable polymer 310 and/or the photoinitiators 318 can be in a liquid form, no more organic or aqueous solvents are needed to prepare the liquid dispersion. In an exemplary embodiment, the liquid dispersion can be formed by ball milling the CNTs 315 (along with the dispersant 317) in a liquid UV curable polymer 310, and then adding the photoinitiators 318 there-into.

In embodiments, the liquid dispersion can then be coated, UV-cured, and then, as desired, for example, as seamless belt, or welded to form a belt.

In an exemplary embodiment, the liquid dispersion can be coated via an extrusion die, flow coating, or other known coating techniques. The coated member can then be introduced into a UV curing chamber to cure the UV curable polymer. The UV-cured polymer can be a seamless belt, or welded, for example, through ultrasound welding to form an exemplary intermediate transfer belt.

Depending on the UV curable polymers and photoinitiators used, the coated liquid dispersion can be UV cured at a wavelength, for example, ranging from about 200 nm to about 400 nm, including from about 240 nm to about 370 nm, or from about 270 nm to about 340 nm.

In embodiments, the cured and/or welded layer (see 250A of FIGS. 3A-3C) can have a thickness ranging from about 1 micron to about 500 microns, from about 30 microns to about 500 microns, or from about 50 microns to about 200 microns, although other thickness can also be included.

In embodiments, due to the small amount and unique dimensions and properties of carbon nanotubes 315, the formed layer 250A of FIGS. 3A-3C can have improved electrical and/or mechanical properties including a uniform resistivity and/or a uniform mechanical module within desired ranges. In embodiments, the uniform resistivity (or modules) can include a uniform resistivity (or modules) between a volume or bulk resistivity (or modules) and a surface resistivity (or modules) of the layer 250A.

In embodiments, the formed intermediate transfer layer 250A of FIGS. 3A-3C can have a surface resistivity of at least about $10^8$ ohms/sq, or ranging from about $10^8$ ohms/sq to about $10^{13}$ ohms/sq, or ranging from about $10^9$ ohms/sq to about $10^{12}$ ohms/sq.

In embodiments, the formed intermediate transfer layer 250A of FIGS. 3A-3C can have a mechanical Young's modulus of at least about 500 MPa, or ranging from about 500 MPa to about 8,000 MPa, or ranging from about 1,000 MPa to about 3,000 MPa.

The following examples are intended to be illustrative, and the present teachings are not limited to the materials, conditions, or process parameters set forth in these examples.

EXAMPLES

Example 1

A nanotube-based dispersion was obtained from Zyvex Performance Materials (Columbus, Ohio). The nanotube-based dispersion contained multi-walled nanotube (MWNT) mixed with a dispersant represented by

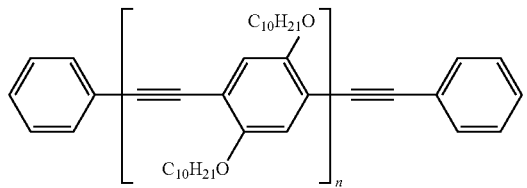

in a solvent of methylene chloride. In this nanotube-based dispersion, MWNT/dispersant had a ratio of 83/17 by weight and the dispersion had solids (including the MWNTs and the dispersant) in an amount of about 78% by weight.

About 100 grams of the above nanotube-based dispersion was mixed with (1) about 111.8 grams of the aromatic urethane acrylate, (2) about 13 grams of the acrylate monomer, and (3) about 4.4 grams of their photoinitiator.

In this mixture, the aromatic urethane acrylate used was commercially available as SARTOMER® CN2901 of urethane triacrylate oligomer (Tg=35° C.) from Sartomer (Exton, Pa.). The acrylate monomer used was commercially available as LAROMER® TMPTA (trimethylolpropane triacrylate) from BASF (Florham Park, N.J.). The photoinitiator used was commercially available as IRGACURE® 651 (a,a-dimethoxy-a-phenylacetophenone) from Ciba Specialty Chemicals (Tarrytown, N.Y.).

A uniform liquid dispersion was then formed by ball milling the above mixture with 2 millimeter stainless shot with an Attritor for 1 hour. The uniform liquid dispersion was then coated on a glass plate using a draw bar coating method, and subsequently cured using a Hanovia UV instrument (Fort Washington, Pa.) for about 40 seconds at a wavelength of about 325 nanometer (125 watts). The film was then released from the glass plate having a thickness of about 100 microns.

The above ITB film of Example 1 was measured for surface resistivity (averaging four to six measurements at varying spots, 72° F./65 percent room humidity) using a High Resistivity Meter (Hiresta-Up MCP-HT450 available from Mitsubishi Chemical Corp.). The surface resistivity was about $2.4 \times 10^9$ ohms/sq, within the functional range of an ITB of from about $10^9$ to about $10^{13}$ ohms/sq.

The above ITB film of Example 1 was measured for Young's modulus following the ASTM D882-97 process. A sample (0.5 inch×12 inch) from Example 1 was placed in the measurement apparatus, the Instron Tensile Tester, and then elongated at a constant pull rate until breaking. The instrument recorded the resulting load versus sample elongation. The modulus was calculated by taking any point tangential to the initial linear portion of this curve and dividing the tensile stress by the corresponding strain. The tensile stress was given by load divided by the average cross sectional area of the test sample.

The Young's modulus of the Example 1 ITB film was measured to be about 2,000 MPa, within the reported modulus range of the thermoplastic ITBs on the market (from about 1,000 to about 3,500 MPa). Examples of these thermoplastic ITBs for comparison are polyester/carbon black ITB (Ricoh, Young's modulus of about 1,200 MPa), polyamide/carbon black ITB (Brother, Young's modulus of about 1,100 MPa), and polyimide/polyaniline ITB (Xerox, Young's modulus of about 3,500 MPa).

Example 2

A UV cured film was formed using the materials and methods described in EXAMPLE 1 but had a thickness of about 10 microns. The UV cured film was made on a conventional belt and had a print test on a Xerox DC5000 printing machine. The printing results on the UV cured film region showed excellent color density and coverage, identical to the printing results on the conventional belt region.

While the present teachings have been illustrated with respect to one or more implementations, alterations and/or modifications can be made to the illustrated examples without departing from the spirit and scope of the appended claims. In addition, while a particular feature of the present teachings may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising." As used herein, the term "one or more of" with respect to a listing of items such as, for example, A and B, means A alone, B alone, or A and B. The term "at least one of" is used to mean one or more of the listed items can be selected.

Notwithstanding that the numerical ranges and parameters setting forth the broad scope of the present teachings are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume values as defined earlier plus negative values, e.g. −1, −1.2, −1.89, −2, −2.5, −3, −10, −20, −30, etc.

Other embodiments of the present teachings will be apparent to those skilled in the art from consideration of the specification and practice of the present teachings disclosed herein. It is intended that the specification and examples be considered as exemplary only, with a true scope and spirit of the present teachings being indicated by the following claims.

What is claimed is:

1. An intermediate transfer member comprising:
an ultraviolet (UV) curable polymer, wherein the UV curable polymer comprises a urethane acrylate;
a photoinitiator being capable of initiating a curing of the UV curable polymer; and
a plurality of carbon nanotubes dispersed in the UV curable polymer, wherein the plurality of carbon nanotubes is about 3% or less by weight of the UV curable polymer after the UV curable polymer containing the dispersed plurality of carbon nanotubes is cured to produce a cured polymer, and wherein the cured polymer has a surface resistivity ranging from about $10^8$ ohms/sq to about $10^{13}$ ohms/sq.

2. The member of claim 1, wherein the cured polymer has a thickness ranging from about 30 microns to about 500 microns.

3. The member of claim 1, wherein the plurality of carbon nanotubes is present in an amount of about 1% or less by weight of the total cured polymer.

4. The member of claim 1, wherein the plurality of carbon nanotubes comprises multi-walled carbon nanotubes, single-walled carbon nanotubes or combinations thereof.

5. The member of claim 1, wherein the urethane acrylate is selected from the group consisting of an aliphatic urethane acrylate, an aromatic urethane acrylate and a combination thereof.

6. The member of claim 1, wherein the urethane acrylate has a molecular weight ranging from about 300 to about 5,000.

7. The member of claim 1, wherein the UV curable polymer further comprises a monomeric acrylate or vinyl selected from the group consisting of trimethylolpropane triacrylate, hexanediol diacrylate, tripropyleneglycol diacrylate, dipropyleneglycol diacrylate, triethyleneglycol divinyl ether, vinyl caprolactam, n-vinyl formamide and a combination thereof.

8. The member of claim 1, wherein the photoinitiator comprises one or more of a first photoinitiator for a surface curing of the UV curable polymer, a second photoinitiator for a bulk curing of the UV curable polymer and a combination thereof.

9. The member of claim 1, wherein the UV curable polymer comprises urethane acrylate and wherein the photoinitiator comprises acyl phosphines, α-hydroxyketones, benzyl ketals, α-aminoketones, or mixtures thereof.

10. An intermediate transfer member comprising:
an ultraviolet (UV) curable polymer, wherein the UV curable polymer comprises a urethane acrylate;
a photoinitiator being capable of initiating a curing of the UV curable polymer;
a plurality of carbon nanotubes dispersed in the UV curable polymer; and
a dispersant disposed to exfoliate and de-bundle the plurality of carbon nanotubes;
wherein the plurality of carbon nanotubes is about 3% or less by weight of the UV curable polymer after the UV curable polymer containing the dispersed plurality of carbon nanotubes is cured to produce a cured polymer, wherein the dispersant is present in an amount ranging from about 5% to about 30% by weight of the plurality of carbon nanotubes, and wherein the cured polymer has a surface resistivity ranging from about $10^8$ ohms/sq to about $10^{13}$ ohms/sq.

11. The member of claim 10, wherein the dispersant has a formula of

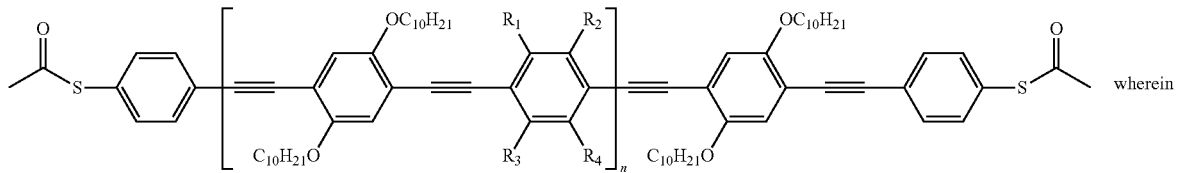

wherein $R_1$ and $R_4$ are H, and $R_2$ and $R_3$ are $OC_{10}H_{21}$,
or
$R_1$, $R_2$, $R_3$ and $R_4$ are X,
or
$R_1$ and $R_4$ are H, and $R_2$ and $R_3$ are

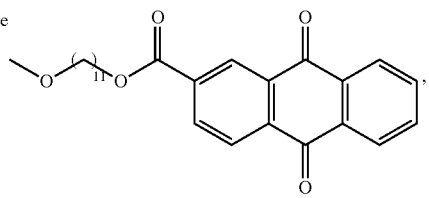

and wherein X is a halide; and n ranges from about 1 to about 225.

12. The member of claim 10, wherein the dispersant has a formula of

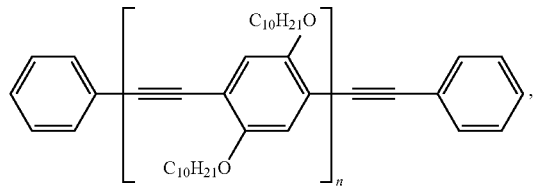

wherein n ranges from about 1 to about 225.

13. The member of claim 1, wherein the cured polymer has a Young's modulus ranging from about 500 to about 3,000 MPa.

14. The member of claim 1 further comprising an outer release layer disposed over the cured polymer.

15. The member of claim 1 further comprising an outer release layer disposed over a conformable layer that is disposed over the cured polymer.

* * * * *